United States Patent [19]
Knapp et al.

[11] Patent Number: 5,830,228
[45] Date of Patent: Nov. 3, 1998

[54] METHODS AND SYSTEMS FOR DEPLOYMENT OF A DETACHABLE BALLOON AT A TARGET SITE IN VIVO

[75] Inventors: Tracey Knapp, Coralville; Michael J. Magliochetti, Iowa City, both of Iowa

[73] Assignee: Urosurge, Inc., Coralville, Iowa

[21] Appl. No.: 654,838

[22] Filed: May 29, 1996

[51] Int. Cl.$^6$ ............................................. A61M 29/00
[52] U.S. Cl. .......................................... 606/195; 604/96
[58] Field of Search ................................. 606/191–192, 606/194, 195; 604/96–101

[56] References Cited

U.S. PATENT DOCUMENTS

| | | |
|---|---|---|
| 2,513,014 | 6/1950 | Fields. |
| 2,856,920 | 10/1958 | Indelicato. |
| 3,795,246 | 3/1974 | Sturgeon. |
| 3,831,585 | 8/1974 | Brondy et al.. |
| 3,834,394 | 9/1974 | Hunter et al.. |
| 4,019,499 | 4/1977 | Fitzgerald. |
| 4,240,433 | 12/1980 | Bordow. |
| 4,282,875 | 8/1981 | Serbinenko et al.. |
| 4,311,146 | 1/1982 | Wonder. |
| 4,327,734 | 5/1982 | White, Jr.. |
| 4,334,327 | 6/1982 | Lyman et al.. |
| 4,341,218 | 7/1982 | Ü. |
| 4,346,712 | 8/1982 | Handa et al.. |
| 4,364,392 | 12/1982 | Strother et al.. |
| 4,395,806 | 8/1983 | Wonder et al.. |
| 4,402,319 | 9/1983 | Handa et al.. |
| 4,429,724 | 2/1984 | Dorros et al.. |
| 4,441,495 | 4/1984 | Hicswa. |
| 4,517,979 | 5/1985 | Pecenka. |
| 4,520,823 | 6/1985 | LeVeen et al.. |
| 4,545,367 | 10/1985 | Tucci. |
| 4,557,255 | 12/1985 | Goodman. |
| 4,559,043 | 12/1985 | Whitehouse et al.. |
| 4,686,962 | 8/1987 | Haber. |
| 4,773,393 | 9/1988 | Haber et al.. |
| 4,802,479 | 2/1989 | Haber et al.. |
| 4,819,637 | 4/1989 | Dormandy, Jr. et al.. |
| 4,832,680 | 5/1989 | Haber et al.. |
| 5,007,898 | 4/1991 | Rosenbluth et al.. |
| 5,071,429 | 12/1991 | Pinchuk et al.. |
| 5,078,681 | 1/1992 | Kawashimma. |
| 5,222,970 | 6/1993 | Reeves .............................. 606/195 |
| 5,304,123 | 4/1994 | Atala et al.. |
| 5,411,475 | 5/1995 | Atala et al.. |

FOREIGN PATENT DOCUMENTS 2185400  7/1987  United Kingdom.

*Primary Examiner*—William Lewis
*Attorney, Agent, or Firm*—Thomas J. Engellenner; Mark D. Russett; Lahive & Cockfield, LLP

[57] ABSTRACT

Methods and systems for deployment of a detachable, inflatable balloon at a target site in vivo are disclosed. In one aspect of the invention, the method involves providing a holder; passing a protective sheath through the lumen of the holder; passing a positioning element through the lumen of the sheath; advancing the positioning element to the target site in vivo; withdrawing the positioning element while keeping the sheath fixed relative to the holder; passing a detachable, inflatable balloon coupled to a distal end of a delivery device through the sheath; withdrawing the sheath into a retractor disposed at proximal end of the delivery device such that the delivery device remains fixed relative to the holder and the balloon is exposed to the target site in vivo; and inflating and detaching the balloon. In another aspect, the system includes a holder; a protective sheath configured for insertion through the holder; a delivery device for carrying a detachable, inflatable balloon disposed at its distal end, the delivery device configured for insertion through the sheath; and a retractor, disposed at a proximal end of the catheter, for withdrawing the sheath whereby the delivery device remains fixed relative to the holder and the balloon is exposed to the target site.

30 Claims, 3 Drawing Sheets

METHODS AND SYSTEMS FOR DEPLOYMENT OF A DETACHABLE BALLOON AT A TARGET SITE IN VIVO

BACKGROUND OF THE INVENTION

The field of this invention concerns the delivery of inflatable, detachable balloons in medical procedures involving blood vessels, body cavities, and the like, and, in particular, in medical procedures involving the treatment of urinary incontinence.

Various techniques have been used for the delivery of detachable balloons. See, for example, Haber et al., U.S. Pat. No. 4,832,680, issued May 23, 1989; U.S. Pat. No. 4,802, 479, issued Feb. 7, 1989; U.S. Pat. No. 4,773,393, issued Feb. 27, 1988; and U.S. Pat. No. 4,686,962, issued Aug. 18, 1987. Haber et al., in particular, describe an extensible inflatable containment membrane which is implanted between the urethra and the subcutaneous corpus spongiousum of a patient to overcome urinary incontinence. The containment membrane of Haber et al. is positioned using a hypodermic needle.

Such devices and methods require complicated devices for stabilizing the delivery of the balloon during the insertion and positioning. Such devices and methods also may require specialized instrumentation to accommodate balloon insertion and positioning with a hypodermic needle.

There exists a need for better methods and systems for accurate delivery of inflatable, detachable balloons. A simple system for stabilizing balloon delivery devices would satisfy a long felt need in the art by reducing the overall procedure time, maximizing the efficacy of the methods and systems and, hence, reducing patient discomfort.

SUMMARY OF THE INVENTION

Methods and devices are disclosed for the deployment of detachable, inflatable balloons at a target site in a patient in vivo. The present invention is based on the recognition that a balloon delivery device can be inserted through a protective sheath which is slidably mounted within a holder. The sheath can be retracted and, if desired, locked, such that the delivery device remains fixed relative to the holder and the balloon is exposed to the target site in vivo.

In one aspect of the invention, a detachable, inflatable balloon is deployed to a target site in vivo according to the following steps. A holder having an inner lumen, a proximal receiving end and a distal exiting end is provided and a protective sheath passed through the holder inner lumen at the proximal receiving end until a distal end of the sheath extends to at least the distal exiting end of the holder. A positioning element is passed through an inner lumen of the sheath until a positioning element tip disposed at a distal end of the positioning element extends beyond the holder's distal exiting end and the distal end of the sheath. The positioning element tip is advanced to the target site in vivo and used to establish a pocket. The positioning element is then withdrawn from the sheath such that the sheath remains fixed relative to the holder. A detachable inflatable balloon coupled to a distal end of a delivery device is passed through the sheath. The sheath is withdrawn into a retractor disposed at a proximal end of the delivery device such that the delivery device remains fixed relative to the holder and the balloon is exposed to the target site in vivo. The balloon is then inflated, preferably with an inert biocompatible material (e.g. a polymerizable solution), and detached at the target site in vivo.

In one embodiment of the invention, the step of withdrawing the sheath into the delivery device retractor can include rotating the delivery device retractor such that a hub disposed at a proximal end of the sheath is withdrawn into the delivery device retractor. In another embodiment, the step of passing the balloon through the sheath can include passing the delivery device retractor over a hub disposed at the proximal end of the sheath until the delivery device retractor contacts a stopper means, disposed on the holder, for preventing passage of the delivery device through the holder beyond a pre-determined point.

In other embodiments, the step of providing the holder can include providing a stabilizing means, such as a flange, disposed at a distal exiting end of the holder, for stabilizing the holder against a surface exterior to the holder. The step of providing the holder can also include providing an outer holder member and an inner holder member, each having an inner lumen, a proximal receiving end and a distal exiting end; and inserting the inner holder member at least partially into the outer holder member to form the holder; and the step of advancing the positioning element tip to the target site in vivo can also include progressively releasing a projection element disposed on the inner holder member into corresponding projection releasing elements disposed on the outer holder member to provide a visual indication of the depth of insertion. The step of progressively releasing a projection element can include depressing a lever arm having a projection tab disposed on the inner holder member below a surface of the outer holder member projection releasing elements. This step can also include indexing the projection tab from one releasing element to another.

In still other embodiments, the step of passing the sheath through the holder can include passing a guide, disposed on the sheath, along a corresponding passageway, disposed on the holder, such that passage of the sheath through the holder is directed along a longitudinal axis relative to the holder. The step of passing the sheath through the holder can also include passing the sheath through the holder until a tab, disposed on the holder, is captured by at least one mating receptacle, disposed on the sheath, thereby inhibiting further movement of the sheath relative to the holder.

In further embodiments, the step of providing a holder can include providing a fitting means, disposed at a distal end of the holder, for providing an attachment to a viewing instrument; providing a sealing means disposed at the distal exiting end of the holder for providing a seal between the holder and a viewing instrument holder inner lumen; and/or providing a viewing instrument capable of attachment to the distal exiting end of the holder, for directly visualizing the target site of a patient in vivo.

In another aspect of the invention, a system for deploying a detachable, inflatable balloon to a target site in vivo is disclosed. The system can include a holder having an inner lumen, a proximal receiving end and a distal exiting end; a protective sheath configured for insertion through the holder inner lumen at the proximal receiving end and extending to at least the distal exiting end of the holder, including a hub disposed at a proximal end of the sheath, and a shaft portion extending outwardly from the hub along a longitudinal axis, the hub and the shaft each having an inner lumen; a delivery device for carrying a detachable, inflatable balloon at its distal end, the delivery device configured for insertion through the sheath; and a retractor disposed at a proximal end of the delivery device for withdrawing the sheath whereby the delivery device remains fixed relative to the holder and the balloon is exposed to the target site.

In other embodiments, the delivery device retractor can include a head for withdrawing the hub of the sheath upon movement of the head. The head can be internally threaded for withdrawing the sheath hub upon rotation of the head. The holder can include a stopper means, disposed close to a proximal end of the holder, for limiting passage of the delivery device through the holder at a pre-determined point; a stabilizing means, such as a flange, disposed at a distal end of the holder, for stabilizing the holder against a surface exterior to the holder; a fitting means, disposed at the distal end of the holder, for providing an attachment to a viewing instrument; and/or a sealing means disposed at the distal exiting end of the holder for providing a seal between the holder and a viewing instrument. The system can further include a viewing instrument capable of attachment to the distal exiting end of the holder, for viewing the placement of the balloon.

In still other embodiments, the system can include a visual indication means, disposed on the holder, for providing a visual indication of a penetration depth of the sheath into the patient; and adjustment means disposed on the holder for adjusting the holder's length. The holder can include an outer holder member having projection releasing elements, an inner holder member having at least one projection element, and the inner holder member fitting at least partially into the outer holder member such that upon advancement of the inner holder member into the outer holder member, the inner holder member projection element is progressively released into the outer holder member projection releasing elements to provide a visual indication of a penetration depth of the sheath in the patient. The inner holder member projection element can include a depressible lever arm having a projection tab, such that the arm can be depressed below a surface of the outer holder member projection releasing elements to provide for indexing of the projection tab from one releasing element to another.

In further embodiments, the system can include a guide disposed on the sheath and a passageway disposed on the holder, such that movement of the guide along the passageway during passage of the sheath through the holder directs the sheath along a longitudinal axis relative to the holder; and a tab, disposed on the holder, and at least one mating receptacle, disposed on the sheath, such that interconnection of the tab with the mating receptacle inhibits movement of the sheath relative to the holder; and/or a positioning element for passage through the sheath prior to passage of the delivery device through the sheath, for establishing a pocket at the target site in vivo.

In still further embodiments, the positioning element can be a needle, such as a hypodermic or a cytoscopic needle or a solid wire. The lumen of the sheath can have an inside diameter from about 0.005 mm to about 7.0 mm. The sheath can also include a visual indication means including graduation markings disposed on the distal end of the sheath, for providing a visual indication of a penetration depth of the sheath into the patient. The delivery device can include an inner catheter enclosed within an outer catheter, the inner catheter having a distal end extending at least to a distal end of the outer catheter.

DETAILED DESCRIPTION

Figure 1:
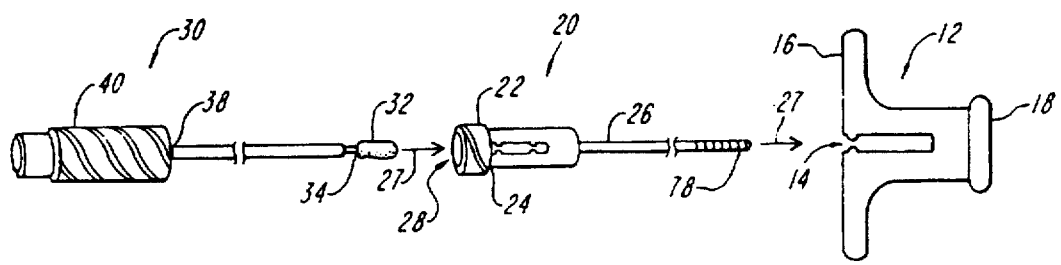
FIG. 1 is an exploded side view of the system including a holder, a protective sheath, and a delivery device according to the invention.

The present invention pertains to methods and systems for the deployment of detachable inflatable balloons to a target site in vivo. The invention involves a delivery device which can be inserted through a protective sheath enclosed in a holder to the target site in vivo. The sheath can be withdrawn such that the delivery device remains fixed relative to the holder and the balloon is exposed to the target site in vivo.

The target site can be a site selected such that the implantation of a detachable balloon would be advantageous to a subject. The target site, for example, can be in close proximity to or within a duct and the purpose of the implantation of the detachable balloon is to block the duct from within or provide external pressure causing partial or complete closure of the duct. For example, the target site can be between the urethra and the subcutaneous corpus spongiousum. Alternatively, the target site can be the subureteral region of a reflux prone bladder.

The methods and systems of this invention can be used, for example, as a means for treating urinary incontinence. The inflated, detached balloon can be placed between the urethra and the subcutaneous corpus spongiousum providing a localized, controlled tissue volume increase. The corpus spongiousum would be expanded, thereby occluding the urethra.

In an additional example, the methods and systems of this invention can be used for the treatment of vesicoureteral reflux. The inflated detached balloon can be placed in the subureteral region of a refluxing bladder (e.g., between the mucosal and submucosal tissue layers). The compressive effect of the inflated balloon can then re-configure the ureteral tunnel so as to minimize the likelihood of reflux.

The present invention can also be used in other types of medical treatments, including, but not limited to, the treatment of gastroesophageal reflux, otolaryngology, reversible sterilization (i.e., in the occlusion of the fallopian tubes and/or the occlusion of the vas deferens), and urinary diverticula.

Balloon structures useful in the present invention can be formed from silicone or similar substantially non antigenic elastic materials. The uninflated balloons preferably are sized to fit into the tip of a catheter which can pass readily through the lumen of a protective sheath. The balloon structures can take various forms but preferably include a sealing mechanism which seals the balloon upon inflation. The sealing mechanism can be achieved, for example, by a constrictive collar, or a lip seal, or both.

For further description of detachable balloon structures useful in the present invention, see commonly owned U.S. Pat. Nos. 5,304,123 and 5,411,475, herein incorporated by reference.

The balloon can be delivered by a delivery device, such as a catheter, which is inserted through the protective sheath enclosed in a holder to the site where the balloon is to be inflated. In one preferred embodiment, the delivery device provides a means for not only inflating the balloon but also means for filling the balloon with a biocompatible material. Catheters suitable for use in the present invention are available from various sources including, for example, TFX Medical (Jaffrey, N. H.).

Various materials can be used to fill the balloon, including collagen, autologous fat or cellular extracts, an inert polymer, contrast media or saline. In one embodiment, the balloon is filled with a polymerizable solution, such as an acrylic solution which solidifies in situ. For example, the polymerizable solution can be a solution of hydroxyethyl methylacrylate (HEMA) which is cured to a solid form by addition of ferrous sulfate and hydrogen peroxide. In another embodiment, the balloon is filled with a hydrogel material such as polyvinyl pyrrolidone.

The invention will next be described in connection with certain illustrated embodiments; however, it should be clear that those skilled in the art can make various modifications, additions and subtractions without departing from the spirit or scope of the invention. For example, although the present invention is illustrated in terms of a target site close to or within a duct, the invention is applicable to other target areas in a body.

FIG. 1 is an exploded side view of system 10 including a holder 12, a protective sheath 20, and a delivery device 30, according to the invention. The holder 12 has an inner lumen 14, a proximal receiving end 16, and a distal exiting end 18. The protective sheath 20 can be configured for insertion through the holder 12 at the proximal receiving end 16 such that it extends at least to the distal exiting end 18 of the holder 12 and can include a hub 22 disposed at the proximal end 24 of the sheath 20, and a shaft portion 26 extending outwardly from the hub 22 along a longitudinal axis 27, the hub 22 and the shaft portion 26 each having an inner lumen 28. The sheath 20 can also include visual indication means 78, such as graduation markings, disposed on the distal end of the shaft portion 26 of the sheath 20 for indicating the penetration depth of the sheath into the patient according to a pre-determined correlation. The delivery device 30 for carrying a detachable, inflatable balloon 32 at its distal end 34, is configured for insertion through the sheath 20 at the hub 22. A retractor 40 is disposed at a proximal end 38 of the delivery device 30 for withdrawing the sheath 20 whereby the device 30 remains fixed relative to the holder 12.

Each of the holder 12, sheath 20 and delivery device 30 can be color coded for easy assembly.

Figure 2:
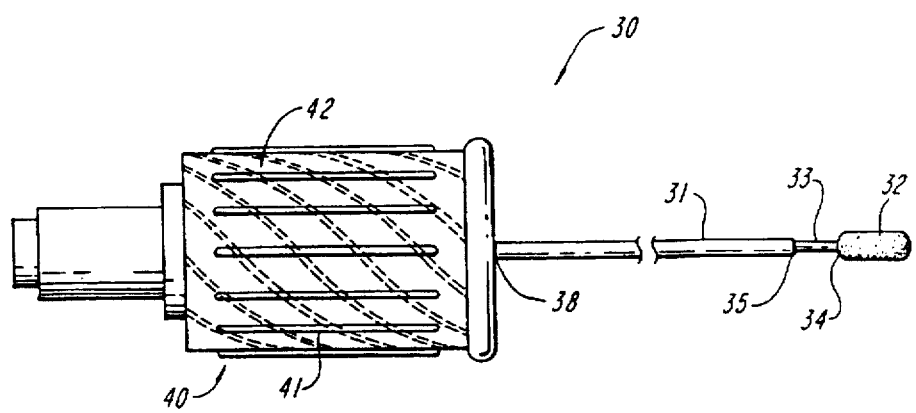
FIG. 2 is a more detailed side view of the retractor component of the delivery device of FIG. 1.

FIG. 2 is a more detailed side view of the retractor 40 component of the delivery device 30. The delivery device retractor 40 includes a head 42 for withdrawing the hub 22 of the sheath 20 upon movement of the head. The head 42 can be internally threaded such that the hub 22 of the sheath 20 is withdrawn upon rotation of the threaded head. The head 42 can also include raised external ridges 41 to aid in gripping and/or rotating the head 42. FIG. 2 also illustrates that the delivery device 30 can include an inner catheter 33 enclosed within an outer catheter 31, the distal end 34 of the inner catheter 33 extending at least to the distal end 35 of the outer catheter 31. Such a two catheter design provides more support for safely transporting the balloon 32 to the desired target site in the patient.

Figure 3A:
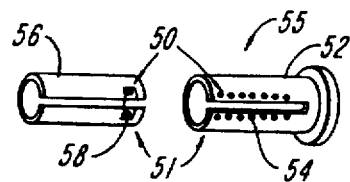
FIG. 3A is an expanded side view of the holder of FIG. 1 having inner and outer holder members.
Figure 3B:
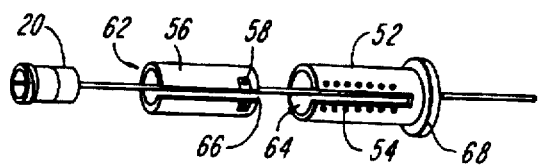
FIG. 3B is an illustration of the passage of a protective sheath through an inner and an outer holder member.
Figure 3C:
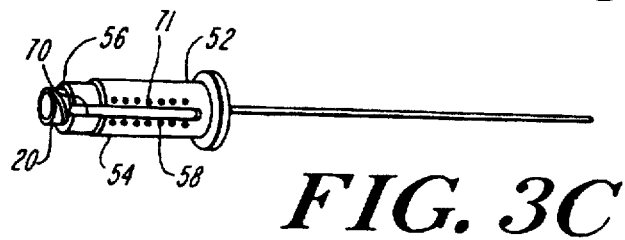
FIG. 3C shows the protective sheath fully inserted into a holder including an inner and an outer holder member.
Figure 3D:
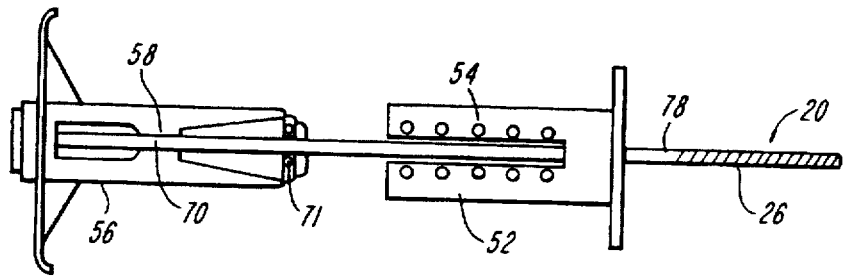
FIG. 3D is an enlarged view of the holder illustrating a projection element including a lever arm having a depressible projection tab.

FIG. 3A illustrates that the system 10 can also include a holder 55 including a visual indication means 50 for providing a visual indication of a penetration depth of the sheath 20 into the patient and an adjustment means 51 for varying the length of the holder. Such a holder 55 can include an outer holder member 52 having projection releasing elements 54 and an inner holder member 56 having at least one projection element 58. FIG. 3B illustrates that the sheath 20 can be inserted into the lumen 62 of the inner holder member 56 and the lumen 64 of the outer holder member 52 such that the sheath 20 extends at least to the distal end 66 of the inner holder member 56 and the distal end 68 of the outer holder member 52. The inner holder member 56 enclosing the sheath 20 can fit at least partially into the outer holder member 52. As the inner holder member 56 enclosing the sheath 20 is further advanced into the outer holder member 52, the projection element 58 is progressively released into the projection releasing elements 54 providing a visual indication of a penetration depth of the sheath 20 into the patient, as shown in FIG. 3C. FIG. 3D illustrates that the projection element 58 of the inner holder member 56 can include a lever arm 70 having a projection tab 71 that can be depressed such that the projection tab 71 is indexed from one releasing element 54 to another during advancement of the inner holder member 56 into the outer holder member 52.

Figure 4:
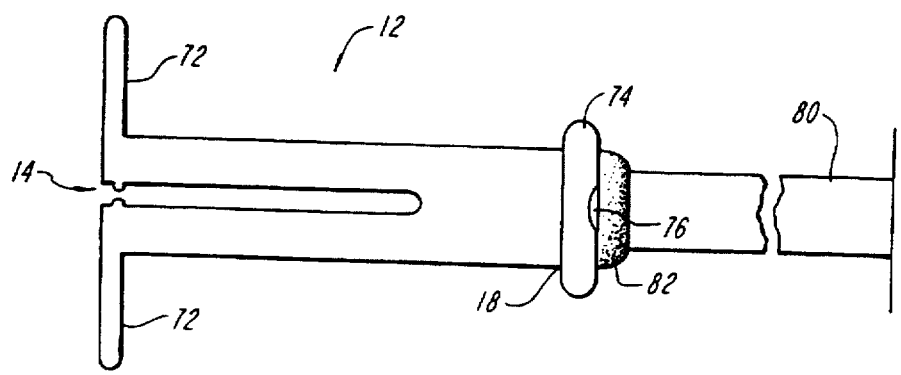
FIG. 4 is a more detailed side view of a holder illustrating a stopper mechanism attached to a viewing instrument according to the invention.

FIG. 4 is a more detailed side view of the holder 12 including a stopper means 72, disposed on the holder 12, for preventing further movement of the delivery device retractor 40 over the holder 12 and thus limiting passage of the delivery device 30 through the holder 12 at a pre-determined point. Stopper means 72 also provides a place for the physician to position his or her index and middle fingers, simplifying maneuvering of the system. FIG. 4 further illustrates a stabilizing means 74, such as a flange, disposed on the distal exiting end 18 of the holder 12, for stabilizing the holder 12 against a surface exterior to the holder 12. The distal exiting end 18 of the holder 12 can also include a fitting means 76 for attachment to a viewing instrument 80. The system 10 can include such a viewing instrument 80 capable of attachment to the distal exiting end of the holder 12. The holder 12 can further include a sealing means 82 disposed at the distal exiting end of the holder 12 for providing a seal between the holder 12 and the viewing instrument 80, thereby preventing the back-flow of fluids into the holder inner lumen. The sealing means 82 can be made of a variety of materials, such as silicone, known to persons familiar with the art.

Thus, for example, in the treatment of urinary incontinence, the protective sheath 20 can be passed through a lumen of a viewing instrument 80 and the viewing instrument can be passed via the urethra to a target site between the urethra and the subcutaneous corpus spongiousum for injection and detachment of the balloon (transurethral delivery). Alternatively, the protective sheath 20 and the viewing instrument 80 can be passed in parallel via the urethra to the target site. In addition, the protective sheath 20 can be passed through the patient's tissue parallel to the urethra to the target site for injection and detachment of the balloon 32 (periurethral delivery). Positioning of the sheath can be observed via a viewing instrument passed through, for example, the urethra.

In an alternative example involving the treatment of vesicoureteral reflux, the protective sheath 20 can be passed through a lumen of a viewing instrument 80 which can be passed through the ureter to a target site (e.g., the subureteral region of a refluxing ureter between the mucosal and submucosal tissue layers).

Various materials can be used for the sheath and/or the positioning element. For example, a flexible material such as nickel titanium is preferable for the sheath and/or the positioning element, when these components are passed through the lumen of a viewing instrument as, for example, during transurethral delivery. When these components are passed through a patient's tissue as, for example, during periurethral delivery, an inflexible material such as stainless steel is preferable.

The viewing instrument of the present invention can be any scope capable of providing direct visualization of a target site. Examples of scopes which are intended to be encompassed by the present invention are endoscopes such as cystoscopes or ureteralscopes. Various cystoscopes can be used in the present invention and are commercially available from various sources including, for example, Karl Storz Co. (Culver, Calif.); and Olympus Corporation of (Wilmington, Mass.). Direct visualization is intended to encompass visualization by the human eye or visualization using a media which is an actual picture of what would be seen by the human eye looking through the scope, e.g. video.

Figure 5A:
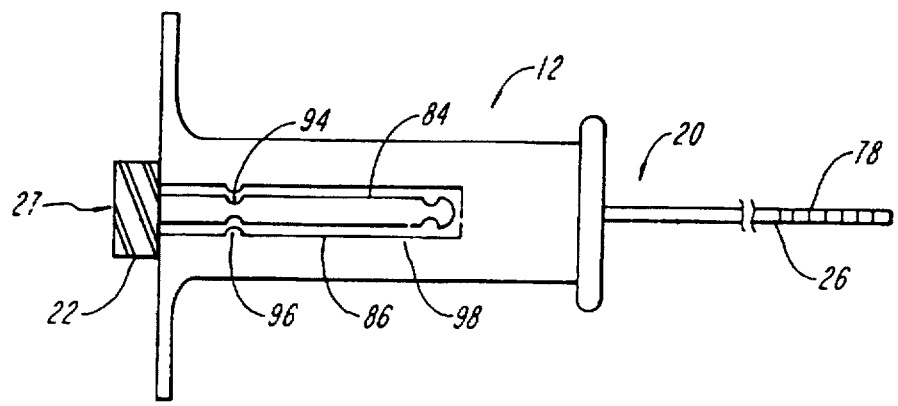
FIG. 5A is a view of a guide of a sheath being advanced along a passageway of a holder.

FIG. 5A illustrates that the system can include a guide 84 on the hub 22 of the sheath 20 which can be advanced along a corresponding passageway 86 on the holder 12, such that passage of the sheath 20 through the holder 12 is directed along a longitudinal axis relative to the holder 12. Such movement of the guide 84 along the passageway 86 also prevents awkward rotation of the sheath 20 about the longitudinal axis of the holder 12..

FIG. 5A further illustrates that the system can include a tab 96 disposed on the holder 12 which can be captured by at least one mating receptacle 94 disposed on the guide 84 of the sheath 20 when the sheath 20 is inserted to a pre-determined extent into the holder 12. In one embodiment, the tab 96 can include two projections disposed on opposing sides of the passageway 86. The insertion of the sheath 20 into the holder 12 including the movement of the guide 84 along the passageway 86 can expand the sides 98 of the passageway 86. When the tab projections 96 are captured by the mating receptacles 94, the passageway sides 98 can retract, resuming their original configuration.

Figure 5B:
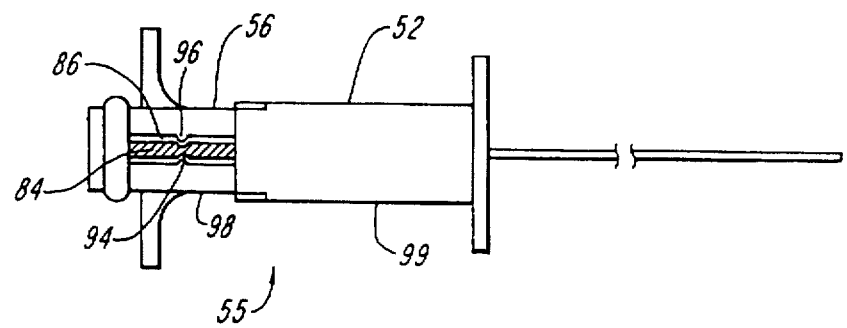
FIG. 5B is a view of a tab disposed along the passageway of a holder having inner and outer holder members, the tab having been captured by a mating receptacle disposed along a guide of a sheath.

When a holder 55 includes inner and outer holder members, as illustrated by FIG. 5B, the sides 99 of the outer holder member 52 can be relatively inflexible as compared to the sides 98 of the passageway 86 of the inner holder member 56. The sheath 20 can be inserted into the inner holder member 56, the sheath guide 84 passed along the passageway 86 of the inner holder member 56, and the tab projections 96 of the sheath 20 captured by the corresponding mating receptacles 94 on the inner holder member 56. The inner holder member 56 can then be inserted into the outer holder member 52. Removal of the sheath 20 from the holder 55 is further limited because the outer holder member sides 99 restrict the sides 98 of the passageway 86 of the inner holder member 56 to expand to allow removal of the captured tab projections 96 from the corresponding mating receptacles 94.

Figure 6:
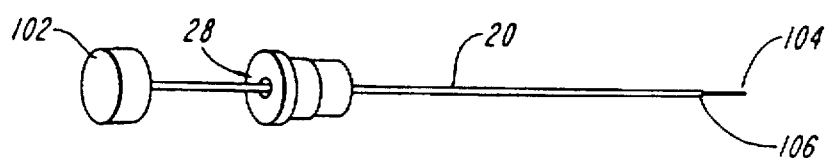
FIG. 6 is a view of a positioning element of the system.

FIG. 6 illustrates that the system can also include a positioning element 102, such as a hypodermic or cytoscopic needle, or a solid wire, which is configured to allow passage through the inner lumen 28 of the sheath 20 until a tip 104 at a distal end 106 of the positioning element 102 extends beyond the distal end of the sheath.

The inner lumen 28 of the sheath 20 can have an inside diameter of about 0.005 mm to about 7.0 mm and the sheath can have a length of about 2.5 cm to about 245 cm. The positioning element 102 can have an outside diameter of about 0.003 mm to about 6.5 mm and a length of about 2.54 cm to about 250 cm. The delivery catheter can have an inside diameter of about 0.002 mm to about 6.5 mm and a length of about 2.5 cm to about 245 cm.

Like the holder, sheath, and delivery device, the positioning element 102 can be color coded to facilitate insertion through the holder.

In sum, the present invention benefits from the recognition that a delivery device can be inserted through a protective sheath enclosed in a holder to the target site in vivo, and the sheath can be withdrawn such that the delivery device remains fixed relative to the holder and the balloon is exposed to the target site in vivo. The methods and systems of the present invention have several advantages over the prior art. Withdrawal of the sheath such that the delivery device remains fixed relative to the holder and the balloon is exposed to tissue provides for stable, simple and accurate balloon deployment at the target site in vivo. Other features of the invention, such as the stopper means and the stabilizing means disposed at the proximal and distal ends of the holder, respectively, and the sheath guide and holder passageway, also contribute to stable and less awkward or cumbersome balloon deployment. Further, deployment of a balloon attached to the distal end of a delivery device via a protective sheath enclosed in a holder eliminates the need for the complicated instrumentation required when such balloons are deployed via hypodermic needles. The two-catheter design for balloon delivery provides more support for safely loading and transporting the balloon to the desired target site in the patient.

It will be understood that the above description pertains to only several embodiments of the present invention. That is, the description is provided by way of illustration and not by way of limitation. For example, other means for withdrawing the sheath such that the catheter remains fixed relative to the holder and the balloon is exposed to tissue can be selected consistent with the present invention. The invention is further characterized according to the following claims.

What is claimed is:

1. A system for deploying a detachable, inflatable balloon to a target site in vivo comprising:

a holder having an inner lumen, a proximal receiving end and a distal exiting end;

a protective sheath configured for insertion through the holder inner lumen at the proximal receiving end and extending to at least the distal exiting end of the holder, including a hub disposed at a proximal end of the sheath, and a shaft portion extending outwardly front the hub along a longitudinal axis, the hub and the shaft each having an inner lumen;

a delivery means for carrying a detachable, inflatable balloon at its distal end, the delivery means configured for insertion through the sheath; and a retractor disposed at a proximal end of the delivery means for withdrawing the sheath whereby the delivery means remains fixed relative to the holder and the balloon is exposed to the target site, the retractor comprising a head for withdrawing the hub of the sheath upon movement of the head.

2. The system of claim 1, wherein the holder further comprises means disposed close to a proximal end of the holder, for limiting passage of the delivery means through the holder at a pre-determined point.

3. The system of claim 1, wherein the holder further comprises means disposed at the distal exiting end of the holder for stabilizing the holder against a surface exterior to the holder.

4. The system of claim 1 further comprising:
   means disposed on the holder, for providing a visual indication of a penetration depth of the sheath into the patient.

5. The system of claim 1, wherein the holder further comprises means disposed at the distal exiting end of the holder for providing an attachment to a viewing instrument.

6. The system of claim 1, wherein the holder further comprises means disposed at the distal exiting end of the holder for providing a seal between the holder and a viewing instrument.

7. The system of claim 1 further comprising:
   a viewing instrument capable of attachment to the distal exiting end of the holder, for viewing the placement of the balloon.

8. The system of claim 1, wherein the lumen of the sheath has an inside diameter of from about 0.005 mm to about 7.0 mm.

9. The system of claim 1, wherein the sheath further comprises means disposed on the sheath, for providing a visual indication of a penetration depth of the sheath into the patient.

10. The system of claim 1, wherein the delivery means further comprises an inner catheter enclosed within an outer catheter, the inner catheter having a distal end extending at least to a distal end at the outer catheter.

11. The system of claim 1, wherein the head of the retractor is threaded for engaging the hub of the sheath.

12. A system for deploying a detachable, inflatable balloon to a target site in vivo comprising:
   a holder having an inner lumen, a proximal receiving end and a distal exiting end;
   a protective sheath configured for insertion through the holder inner lumen at the proximal receiving end and extending to at least the distal exiting end of the holder, including a hub disposed at a proximal end of the sheath, and a shaft portion extending outwardly from the hub along a longitudinal axis, the hub and the shaft each having an inner lumen;
   a delivery means for carrying a detachable, inflatable balloon at its distal end, the delivery means configured for insertion through the sheath; and
   a retractor disposed at a proximal end of the delivery means for withdrawing the sheath whereby the delivery means remains fixed relative to the holder and the balloon is exposed to the target site;
   wherein the holder further comprises an outer holder member having a plurality of projection releasing elements, an inner holder member having at least one projection element, and the inner holder member fitting at least partially into the outer holder member such that upon advancement of the inner holder member into the outer holder, the inner holder projection element is progressively released into the projection releasing elements to provide a visual indication of the penetration depth of the sheath into the patient.

13. The system of claim 12, wherein the inner holder member further comprises a depressible lever arm having a projection tab, such that the arm is depressed below a surface of the outer holder member projection releasing elements to provide for indexing from one releasing element to another.

14. A system for deploying a detachable, inflatable balloon to a target site in vivo comprising:
   a holder having an inner lumen, a proximal receiving end and a distal exiting end;
   a protective sheath configured for insertion through the holder inner lumen at the proximal receiving end and extending to at least the distal exiting end of the holder, including a hub disposed at a proximal end of the sheath, and a shaft portion extending outwardly from the hub along a longitudinal axis, the hub and the shaft each having an inner lumen;
   a delivery means for carrying a detachable, inflatable balloon at its distal end, the delivery means configured for insertion through the sheath;
   a retractor disposed at a proximal end of the delivery means for withdrawing the sheath whereby the delivery means remains fixed relative to the holder and the balloon is exposed to the target site; and
   a guide disposed on the sheath and a passageway disposed on the holder, such that movement of the guide along the passageway during passage of the sheath through the holder directs passage of the sheath along a longitudinal axis relative to the holder.

15. A system for deploying a detachable, inflatable balloon to a target site in vivo comprising:
   a holder having an inner lumen, a proximal receiving end and a distal exiting end;
   a protective sheath configured for insertion through the holder inner lumen at the proximal receiving end and extending to at least the distal exiting end of the holder, including a hub disposed at a proximal end of the sheath, and a shaft portion extending outwardly from the hub along a longitudinal axis, the hub and the shaft each having an inner lumen;
   a delivery means for carrying a detachable, inflatable balloon at its distal end, the delivery means configured for insertion through the sheath;
   a retractor disposed at a proximal end of the delivery means for withdrawing the sheath whereby the delivery means remains fixed relative to the holder and the balloon is exposed to the target site; and
   a tab disposed on the holder and at least one mating receptacle disposed on the sheath, such that interconnection of the tab with the mating receptacle inhibits movement of the sheath relative to the holder.

16. A system for deploying a detachable, inflatable balloon to a target site in vivo comprising:
   a holder having an inner lumen, a proximal receiving end and a distal exiting end;
   a protective sheath configured for inserting through the holder inner lumen at the proximal receiving end and extending to at least the distal exiting end of the holder, including a hub disposed at a proximal end of the sheath, and a shaft portion extending outwardly from the hub along a longitudinal axis, the hub and the shaft each having an inner lumen;
   a delivery means for carrying a detachable, inflatable balloon at its distal end, the delivery means configured for insertion through the sheath;
   a retractor disposed at a proximal end of the delivery means for withdrawing the sheath whereby the delivery means remains fixed relative to the holder and the balloon is exposed to the target site; and
   a positioning element for passage through the sheath prior to passage of the delivery means through the sheath, for establishing a pocket at the target site in vivo.

17. The system of claim 16, wherein the positioning element is a needle.

18. A method of deploying a detachable, inflatable balloon at a target site in a patient in vivo, comprising:

providing a holder having an inner lumen, a proximal receiving end and a distal exiting end;

passing a protective sheath through the holder inner lumen at the proximal receiving end until a distal end of the sheath extends to at least the distal exiting end of the holder;

passing a positioning element through an inner lumen of the sheath until a positioning element tip disposed at the distal end of the positioning element extends beyond the holder distal exiting end and the distal end of the sheath;

advancing the positioning element tip to the target site of the patient in vivo to establish a pocket at the target site in vivo;

withdrawing the positioning element from the sheath such that the sheath remains fixed relative to the holder;

passing a detachable inflatable balloon coupled to a distal end of a delivery means through the sheath;

withdrawing the sheath with a retractor disposed at a proximal end of the delivery means such that the delivery means remains fixed relative to the bolder and the balloon is exposed to the target site in vivo; and inflating and detaching the balloon at the target site in vivo.

19. The method of claim 18, wherein the step of withdrawing the sheath into the delivery means retractor further comprises moving the retractor such that a hub disposed at a proximal end of the sheath is withdrawn into the retractor.

20. The method of claim 18, wherein the step of passing the balloon through the sheath further comprises passing the delivery means retractor over a hub disposed at the proximal end of the sheath until the delivery means retractor contacts means disposed on the holder, for preventing passage of the delivery means through the holder beyond a predetermined point.

21. The method of claim 18, wherein the step of providing the holder further comprises providing means disposed at the distal exiting end of the holder, for stabilizing the holder against a surface exterior to the holder.

22. The method of claim 18, wherein the step of providing a holder further comprises providing an outer holder member and an inner holder member, each having an inner lumen, a proximal receiving end and a distal exiting end; and inserting the inner holder element at least partially into the outer holder member forming the holder; and the step of advancing the positioning element tip to the target site in vivo further comprises progressively releasing a projection element disposed on the inner holder member into a plurality of corresponding projection releasing elements disposed on the outer holder member to provide a visual indication of the depth of insertion.

23. The method of claim 22, wherein the step of progressively releasing a projection element disposed on the inner holder member into corresponding outer holder member projection releasing elements further comprises depressing a lever arm having a projection tab below a surface of the outer holder member projection releasing elements and indexing the projection tab from one releasing element to another.

24. The method of claim 18, wherein the step of passing the sheath through the holder further comprises passing a guide disposed on the sheath along a corresponding passageway disposed on the holder such that passage of the sheath through the holder is directed along a longitudinal axis relative to the holder.

25. The method of claim 18, wherein the step of passing the sheath through the holder further comprises passing the sheath through the holder until a tab disposed on the holder is captured by at least one mating receptacle disposed on the sheath, thereby inhibiting further movement of the sheath relative to the holder.

26. The method of claim 18, wherein the step of providing a holder further comprises providing means disposed at the distal end of the holder for attachment to a viewing instrument.

27. The method of claim 18, wherein the step of providing a holder further comprises providing means disposed at the distal exiting end of the holder for providing a seal between the holder and a viewing instrument.

28. The method of claim 18, further comprising the step of:

providing a viewing instrument capable of attachment to the distal exiting end of the holder for directly visualizing the target site of a patient in vivo.

29. The method of claim 18, wherein the step of withdrawing the sheath with a retractor comprises moving a head of the retractor such that the sheath is withdrawn.

30. The method of claim 29, wherein upon movement of the head, the head threadedly engages a hub of the sheath.

* * * * *